(12) United States Patent
Basu et al.

(10) Patent No.: US 8,524,677 B2
(45) Date of Patent: Sep. 3, 2013

(54) DNA VACCINE AS IMMUNOPROPHYLAXIS AGAINST KALA-AZAR

(75) Inventors: Rajatava Basu, Kolkata (IN); Syamal Roy, Kolkata (IN)

(73) Assignee: Council of Scientific and Industrial Research, New Delhi (IN)

( * ) Notice: Subject to any disclaimer, the term of this patent is extended or adjusted under 35 U.S.C. 154(b) by 965 days.

(21) Appl. No.: 11/685,413

(22) Filed: Mar. 13, 2007

(65) Prior Publication Data
US 2008/0145385 A1 Jun. 19, 2008

Related U.S. Application Data

(60) Provisional application No. 60/781,329, filed on Mar. 13, 2006.

(51) Int. Cl.
*A61K 48/00* (2006.01)
*C12N 15/74* (2006.01)

(52) U.S. Cl.
USPC .................................... 514/44 R; 435/320.1

(58) Field of Classification Search
None
See application file for complete search history.

(56) References Cited

PUBLICATIONS

Basu et al. J Immunol 2005;174:7160-71.*
Mukhopadhyay et al. Vaccine 1999;17:291-300.*
Ramirez et al. Vaccine 2001;20:455-61.*
Melby et al. Infect Immunity 1998; 66:2135-42.*
Edgar M. Carvalho et al. "Cell-Mediated Immunity in American Visceral Leishmaniasis: Reversible Immunosuppression During Acute Infection", Infection and Immunity, vol. 33, No. 2, Aug. 1981, pp. 498-502.
Edgar M. Carvalho et al., "Absence of Gamma Interferon and Interleukin 2 Production during Active Visceral Leishmaniasis", J. Clin. Invest. 76, 1985, pp. 2066-2069.
Vincente Pintado MD et al., "Visceral Leishmaniasis in Human Immunodeficiency Virus (HIV)-Infected and Non-HIV-Infected Patients", Medicine, vol. 80, No. 1, 2001, pp. 54-73.
Peter C. Melby et al., "Identification of Vaccine Candidates for Experimental Visceral Leishmaniasis by Immunization with Sequential Fractions of a cDNA Expression Library", Infection and Immunity, vol. 68, No. 10, Oct. 2000, pp. 5595-5602.
Dimitris A.Kafetzis et al., "Visceral leishmaniasis in paediatrics", Current Opinion in Infectious Diseases, 2002, 15:289-294.
Henry M. Murray, "Clinical and Experimental Advances in Treatment of Visceral Leishmaniasis", Antimicrobial Agents and Chemotherapy, vol. 45, No. 8, Aug. 2001, pp. 2185-2197.
S. Sundar et al., "Failure of Pentavalent Antimony in Visceral Leishmaniasisin India: Report from the Center of the Indian Epidemic", Clinical Infectious Diseases, 2000:31:1104-1107.
Jose M. Perez-Victoria et al., "Alkyl-Lysophospholipid Resistance in Multidrug-Resistant *Leishmania tropica* and Chemosensitization by a Novel P-Glycoprotein-Like Transported Modulator", Antimicrobial Agents and Chemotherapy, vol. 45, No. 9, Sep. 2001, pp. 2468-2474.
Peter C. Melby et al., "Cloning of Syrian Hamster (*Mesocricetus auratus*) Cytokine cDNAs and Analysis of Cytokine mRNA Expression in Experimental Visceral Leishmaniasis", Infection and Immunity, vol. 66, No. 5, May 1998, pp. 2135-2142.
Amanda Jardim et al., "Cloning and structure—function analysis of the *Leishmania donovani* kinetoplastid membrane protein-11", J. Biochem, 305, (1995), pp. 315-320.
Amanda Jardim et al., "Isolation and structural characterization of the *Leishmania donovani* kinetoplastid membrane protein-11, a major immunoreactive membrane glycoprotein", J. Biochem., 305, (1995), pp. 307-313.
Christof Berberich et al., "The expression of the *Leishmania infantum* KMP-11 protein is developmentally regulated and stage specific", Biochimica et Biophysica Acta 1442 (1998) 230-237.
Srirupa Mukhopadhyay et al., "Immunoprophylaxis and immunotherapy against experimental visceral leishmaniasis", Vaccine 17 (1999) pp. 291-300.
J.A.L. Kurtzhals et al., "Dichotomy of the human T cell response to *Leishmania* antigens. II. Absent or Th2-like response to gp63 and Th1-like response to lipophosphoglycan-associated protein in cells from cured viseral leishmaniasis patients", Clin. Exp. Immunol. 1994, 96:416-421.
Jose M. Requena et al., "Immune and clinical parameters associated with *Leishmania infantum* infection in the golden hamster model", Veterinary Immunology and Immunopathology, 76 (2000) 269-281.
M. Kemp et al., "Dichotomy of the human T cell response to *Leishmania* antigens. I. Th1-like response to *Leishmania major* promastigote antigens in individuals recovered from cutaneous leishmaniasis", Clin. Exp. Immunol. 1994: 96:410-415.
Paul M. Kaye et al., "Differential Production of Th1- and Th2-Derived Cytokines does not Determine the Genetically Controlled or Vaccine-Induced Rate of Cure in Murine Visceral Leishmaniasis", The Journal of Immunology, vol. 146, No. 8, Apr. 15, 1991, pp. 2763-2770.
K. Kemp et al., "*Leishmania*-specific T cells expressing interferon-gamma (IFN-γ) and IL-10 upon activation are expanded in individuals cured of visceral leishmaniasis", Clin. Exp. Immunol. 1999; 116:500-504.
Kare Kemp, "Cytokine-Producing T Cell Subsets in Human Leishmaniasis", Archivum Immunologiae et Therapiae Experimentalis, 2000, 48, 173-176.
Peter C. Melby et al, "The Hamster as a Model of Human Visceral Leishmaniasis: Progressive Disease and Impaired Generation of Nitric Oxide in the Face of a Prominent Th1-Like Cytokine Response", The Journal of Immunology, 2001, pp. 1912-1920.
D. Xu et al., "Protection against leishmaniasis by injection of DNA encoding a major surface glycoprotein, gp63, of *L. major*", Immunology 1995, 84, pp. 173-176.

(Continued)

*Primary Examiner* — Janice Li
(74) *Attorney, Agent, or Firm* — Foley & Lardner LLP

(57) ABSTRACT

A highly conserved membrane protein present in all species of *Leishmania* can be used as a vaccine antigen for genetic immunization against visceral leishmananiasis.

10 Claims, 8 Drawing Sheets

(56) References Cited

PUBLICATIONS

J. P. Haldar et al., "Cell-Mediated Immune Response in Indian Kala Azar and Post-Kala Azar Dermal Leishmaniasis", Infection and Immunity, vol. 42, No. 2, Nov. 1983, pp. 702-707.

Edgar M. Carvalho et al., "Restoration of IFN-γ Production and Lymphocyte Proliferation in Visceral Leishmaniasis", Journal of Immunology, 1994, pp. 5949-5956.

Chaltu Gifawesen et al., "Comparison of T-Cell Responses in Self-Limiting versus Progressive Visceral *Leishmania donovani* Infections in Golden Hamsters", Infection and Immunology vol. 57, No. 10, 1989, pp. 3091-3096.

Adam D. Cohen et al., "Modulating the immune response to genetic immunization", The FASEB Journal, vol. 12, Dec. 1998, pp. 1611-1626.

Ruobing Wang et al., "Induction of Antigen-Specific Cytotoxic T Lymphocytes in Humans by a Malaria DNA Vaccine", Science, vol. 282, 1998, pp. 476-480.

Michael Kemp et al., "*Leishmania donovani*-Reactive Th1- and Th2-Like T-Cell Clones from Individuals Who Have Recovered from Visceral Leishmaniasis", Infection and Immunity, vol. 61, No. 3, Mar. 1993, pp. 1069-1073.

Markus Schneemann et al., Nitric Oxide Synthase is Not a Constituent of the Antimicrobial Armature of Human Mononuclear Phagocytes, The Journal of Infectious Diseases, 1993; 167:1358-1363.

Vinod Bhakuni et al., "Immunochemotherapy for *Leishmania donovani* Infection in Golden Hamsters: Combinatorial Action of Poly ICLC Plus L-Arginine and Sodium Stibogluconate (Stibanate®)", Journal of Interferon and Cytokine Research 19:1103-1106 (1999).

Shawn J. Green et al., "*Leishmania major* Amastigotes Initiate the L-Arginine-Dependent Killing Mechanism in IFN-γ-Stimulated Microphages by Induction of Tumor Necrosis Factor-α", The Journal of Immunology, vol. 145, No. 12, Dec. 1990, pp. 4290-4297.

F.Y. Liew et al., "Tumor Necrosis Factor-α Synergizes With IFN-γ in Mediating Killing of *Leishmania major* Through the Induction of Nitric Oxide", The Journal of Immunology, vol. 145, No. 12, Dec. 15, 1990, pp. 4306-4310.

F.Y. Liew et al., "Tumour necrosis factor (TNF-α) in leishmaniasis II. TNF-α-Induced Macrophage Leishmanicidal Activity is Mediated by Nitric Oxide From L-Arginine", Immunology 1990, 71, pp. 556-559.

Xiao-qing Wei et al., "Altered immune responses in mice lacking inducible nitric oxide synthase", Nature, vol. 375, Jun. 1, 1995, pp. 408-411.

Michael U. Shiloh et al., "Phenotype of Mice and Macrophages Deficient in Both Phagocyte Oxidase and Inducible Nitric Oxide Synthase", Immunity, vol. 10, Jan. 1999, pp. 29-38.

Ferric C. Fang, "Perspective Series: Host/Pathogen Interactions Mechanisms of Nitric Oxide—related Antimicrobial Activity", J. Clin. Invest. vol. 99, No. 12, Jun. 1997, pp. 2818-2825.

Sanjay Gurunathan et al., "Vaccination with DNA Encoding the Immunodominant LACK Parasite Antigen Confers Protective Immunity to Mice Infected with *Leishmania major*", The Journal of Experimental Medicine, vol. 186, No. 7, Oct. 6, 1997, pp. 1137-1147.

Christof Berberich et al., "Cloning of Genes and Expression and Antigenicity Analysis of the *Leishmania infantum* KMP-11 Protein", Experimental Parasitology 85, 105-108 (1997).

Edmond P. Walsh et al., "Recombinant Rinderpest Vaccines Expression Membrane-Anchored Proteins as Genetic Markers: Evidence of Exclusion of Marker Protein from the Virus Envelope", Journal of Virology, vol. 74, No. 21, Nov. 2000, pp. 10165-10175.

* cited by examiner

SEQUENCE LISTING

<160> NUMBER OF SEQ ID NOS: 8

<210> SEQ ID NO 1
<211> LENGTH: 390
<212> TYPE: DNA
<213> ORGANISM: Leishmania donovani

<400> SEQUENCE: 1

```
gcgctttctg tttgccttcg atcctcgctc aacgtgcgca taacacactc tcctttcacg      60
cgctcgactt tttccttcca cccctcccc gtgtaaacca tggccaccac gtacgaggag     120
ttttcggcga agctggaccg cctggatcag gagttcaaca ggaagatgca ggagcagaac     180
gccaagttct tgcggacaa gccggatgag tcgacgctgt cgcccgagat gagagagcac     240
```

```
tacgagaagt tcgagcgcat gatcaaggaa cacacagaga agttcaacaa gaagatgcac    300
gagcactcgg agcacttcaa gcagaagttc gccgagctgc tcgagcagca gaaggctgcg    360
cagtacccgt ccaagtaaga tcaggaccac                                    390
```

```
<210> SEQ ID NO 2
<211> LENGTH: 92
<212> TYPE: PRT
<213> ORGANISM: Leishmania donovani

<400> SEQUENCE: 2

Met Ala Thr Thr Tyr Glu Glu Phe Ser Ala Lys Leu Asp Arg Leu Asp
 1               5                  10                  15

Gln Glu Phe Asn Arg Lys Met Gln Gln Asn Ala Lys Phe Phe Ala
             20                  25                  30

Asp Lys Pro Asp Glu Ser Thr Leu Ser Pro Glu Met Arg Glu His Tyr
         35                  40                  45

Glu Lys Phe Glu Arg Met Ile Lys Glu His Thr Glu Lys Phe Asn Lys
     50                  55                  60

Lys Met His Glu His Ser Glu His Phe Lys Gln Lys Phe Ala Glu Leu
 65                  70                  75                  80

Leu Glu Gln Gln Lys Ala Ala Gln Tyr Pro Ser Lys
                 85                  90

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atggccacca cgtacgagga g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttacttggac gggtactggg c                                              21

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctggttccgg cgaatggcca ccacgtacga ggag                                34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
ctcgctccgg cgattacttg gacgggtact gcgc                              34

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggatgatg atatcgccga g                                            21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catgaagcat ttgcggtgga c                                            21
```

DNA VACCINE AS IMMUNOPROPHYLAXIS AGAINST KALA-AZAR

CROSS-REFERENCE TO A RELATED APPLICATION

This application claims the benefit of U.S. Provisional Application No. 60/781,329, filed Mar. 13, 2006, incorporated herein by reference in its entirety.

BACKGROUND OF THE INVENTION

Leishmaniasis, caused by the most-genetically diverse intracellular protozoan parasite, is exemplified by its diversity and complexity. Visceral leishmaniasis (VL), also known as Kala-azar, is caused by members of *L. donovani* (LD) complex resulting in clinical symptoms like fever, cachexia, hepatosplenomegaly, and blood cytopenia. Active VL is associated with the absence of parasite specific cell mediated immune response. Carvalho, E. M., et al. *Infect. Immun.* 33:498. (1981); Carvalho, E. M. et al., *A J. Clin. Invest.* 76:2066. (1985). VL has also been increasingly recognized as an opportunistic infection in individuals infected with HIV virus. Pintado et al. Visceral leishmaniasis in human immunodeficiency virus (HIV)-infected and non-HIV-infected patients. A comparative study, Medicine (Baltimore); 80:54 (2001). The WHO has identified leishmaniasis as a major and increasing public health problem. United Nations Development Program/World Bank/World Health Organization, The Leishmaniasis. WHO Special Program for Research and Training in Tropical Diseases. Ninth Program Report. Tropical diseases: progress in international research, 1987-1988 (1989). Visceral form of leishmaniasis is fatal if left untreated with recent epidemics in Sudan and India resulting in more than 100000 deaths. Melby, P. C., et al., *Infect. Immun.* 68: 5595 (2000).

Failure of the pentavalent antimonials, presently the main form of chemotherapeutic treatment worldwide, is attributed to the emergence of antimony resistant *Leishmania* strains resulting in frequent relapses after treatment. Kafetzis, et al. *Curr. Opin. Infect. Dis.* 15:289 (2002); Murray, H. W., *Antimicrob. Agents Chemother.* 45:2185 (2001). In India, antimony is no longer useful as a drug as 65% of VL patients fail to respond or promptly relapse Sundar, S., D, et al. *Clin. Infect. Dis.* 31:1104 (2000). Alternative chemotherapeutic treatments with amphotericin B and its lipid formulation have severe limitations due to toxic effect and prohibitive high cost of treatment Murray, H. W., *Antimicrob. Agents Chemother:* 45:2185 (2001). An in vitro study has shown that *Leishmania* also developed resistance against Miltefosine, a recently approved effective oral drug for treatment of VL. Perez-Victoria, *Antimicrob. Agents Chemother.* 45(9): 2468 (2001). Growing limitations in available chemotherapeutic strategies due to emerging resistant strains and lack of an effective vaccine strategy against VL deepens the crisis.

Accordingly, there is a need for a vaccine as a possible prophylactic approach against visceral Leishmaniasis.

SUMMARY OF THE INVENTION

In one aspect, the invention provides a method for prophylactic immunizing a mammal infected with virulent form of the parasite *Leishmania*, comprising administering to the mammal a DNA vaccine comprising of (a) cDNA of the antigen known as Kinetoplastid Membrane Protein-11 (KMP-11), (b) cDNA is a polynucleotide comprising a coding region encoding the antigen, wherein the antigen is a cell surface membrane protein of *Leishmania* where prophylactic administration of the vaccine is effective to confer protection to the mammal from the parasite.

In one embodiment, the *Leishmania* is *L. donovani*. In another embodiment, the infected mammal is a Syrian hamster.

In one embodiment, the vaccine stimulates a CD8+ cytotoxic T cell response. In another embodiment, the DNA vaccine comprises an antigen comprising a nucleotide coding region encoding an immunogenic polypeptide.

In another aspect, the invention provides a method for prophylactic immunization of a mammal harboring a lethal dose of *Leishmania* infection comprising: administering to the infected mammal a DNA vaccine comprising a membrane protein of *Leishmania* parasites consisting of (a) an antigen known as Kinetoplastid Membrane Protein-11 (KMP-11), (b) the antigen is a polynucleotide comprising a nucleotide coding region; wherein the antigen comprises of a cell surface protein of *Leishmania* and wherein prophylactic administration of the vaccine is effective to prevent mortality of the mammals from lethal *Leishmania* infection.

In one embodiment, the *Leishmania* is *L. donovani*.

In another embodiment, the vaccine confers sterile protection where parasites were not detected in spleen and livers of the infected mammals. In another embodiment, the DNA vaccine comprises an antigen consisting of a nucleotide coding region encoding an immunogenic polypeptide.

In another aspect, the invention provides a method for prophylactic immunization of a mammal harboring a persistent *Leishmania* infection comprising: administering to the infected mammal a vaccine comprising of coding region of a cell surface protein (a) an antigen known as Kinetoplastid Membrane Protein-11 (KMP-11) (b) a polynucleotide comprising a nucleotide coding region encoding the antigen, wherein the vaccine stimulates an antibody response, a vigorous CTL response, T-cell proliferative response, reduction of splenic and liver parasite burden along with preventing mortality against the *Leishmania* upon prophylactic vaccination to a mammal; wherein the DNA vaccine comprises of an antigen containing nucleotide coding region encoding immunogenic protein and wherein administration of the vaccine is effective to eliminate the parasite from the mammal.

In another aspect, the invention provides a method for prophylactic immunization of mammal harboring a lethal dose of *Leishmania* infection comprising: administering to the infected mammal a vaccine comprising of an antigen consisting (a) of immunogenic polypeptide and (b) a polynucleotide comprising a nucleotide coding region encoding an immunogenic polypeptide, wherein the vaccine stimulates an antibody response, a vigorous CTL response, T-cell proliferative response, reduction of splenic and liver parasite burden along with preventing mortality against the *Leishmania* upon prophylactic vaccination to a mammal; wherein the DNA vaccine comprises of an antigen containing nucleotide coding region encoding immunogenic protein and wherein administration of the vaccine is effective to eliminate the parasite from the mammal.

In another aspect, the invention provides a method for prophylactic immunization of mammal harboring a lethal dose of *Leishmania* infection comprising: administering to the infected mammal a vaccine comprising of an antigen consisting (a) an immunogenic polypeptide known as Kinetoplastid Membrane Protein-11 (KMP-11) (b) a polynucleotide comprising a nucleotide coding region encoding an immunogenic polypeptide, wherein the vaccine stimulates an antibody response, a vigorous CTL response, T-cell proliferative response, reduction of splenic and liver parasite burden along with preventing mortality against the *Leishmania* upon prophylactic vaccination to a mammal; and a mixed Th1/Th2 response wherein the DNA vaccine comprises of an antigen containing nucleotide coding region encoding immunogenic protein and wherein administration of the vaccine is effective to eliminate the parasite from the mammal.

In one embodiment, the mammal is a hamster and has the potential for trials of prophylactic application to primates and humans in future.

DETAILED DESCRIPTION OF THE PREFERRED EMBODIMENTS

Figure 1:
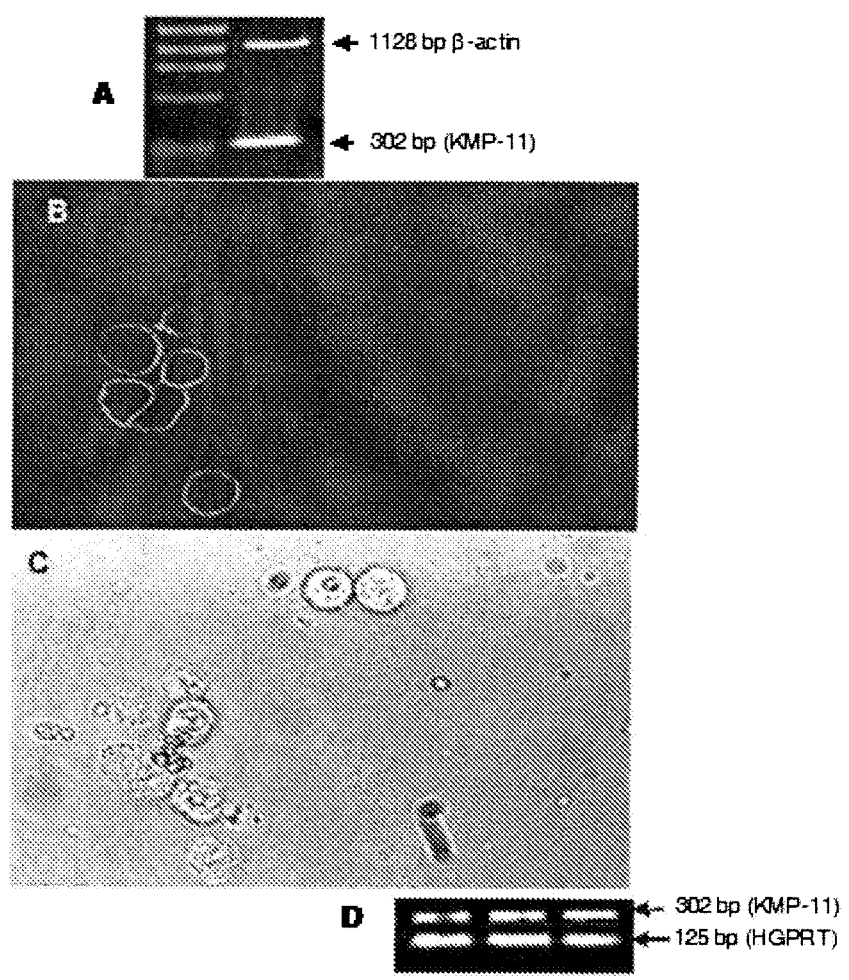
FIG. 1: In vitro and in vivo analysis of KMP-11 expression.

A realistic assessment of efficacy of vaccine against Leishmaniasis depends upon three important variables that we considered in our study—(i) genetic make up of the host; (ii) nature of the antigen tested; and (iii) nature of vaccine. Considering the first variable, our goal of formulating a vaccine strategy was based on its implementation in golden hamster model as they largely reflect clinicopathological features of progressive human VL, showing a relentless increase in visceral burden, progressive cachexia, hepatosplenomegaly, pancytopenia, hypergammaglobulinemia and ultimately death Melby, P. C., V. V. Tryon, B. Chandrasekar, and G. L. Freeman. 1998. Cloning of Syrian hamster (*Mesocricetus auratus*) cytokine cDNAs and analysis of cytokine mRNA expression in experimental visceral leishmaniasis. *Infect. Immun.* 66:2135.

Addressing the second variable was based on selection of KMP-11 as a vaccine candidate antigen. Kinetoplastid Membrane Protein-11 (KMP-11), a highly conserved surface membrane protein present in all members of the family Kinetoplastidae, is differentially expressed both in amastigote and promastigote forms of *Leishmania* Jardim, A., S. Hanson, B. Ullman, W. D. McCubbin, C. M. Kay, and R. W. Olafson. 1995. Cloning and structure-function analysis of the *Leishmania donovani* kinetoplastid membrane protein-11. *Biochem. J.* 305:315. Jardim, A., V. Funk, R. M. Caprioli, and R. W. Olafson. 1995. Isolation and structural characterization of the *Leishmania donovani* kinetoplastid membrane protein-11, a major immunoreactive membrane glycoprotein. *Biochem. J* 305:307. Berberich, C., G. Machado, G. Morales, G. Carrillo, A. Jimenez-Ruiz, and C. Alonso. 1998. The expression of the *Leishmania infantum* KMP-11 protein is developmentally regulated and stage specific. *Biochim. Biophys. Acta*. 1442:230.

In a previous report, we have implicated towards an association of KMP-11 expression with the vaccine potential of an attenuated, avirulent *Leishmania* strain-UR6 Mukhopadhyay, S., P. Sen, S. Bhattacharyya, S. Majumdar, and S. Roy. 1999. Immunoprophylaxis and immunotherapy against experimental visceral leishmaniasis. *Vaccine*. 17: 291. Moreover, ability of KMP-11 to induce IFN-γ from PBMC derived from cured Kenyan VL patients has been reported Kurtzhals, J. A., A. S. Hey, A. Jardim, M. Kemp, K. U. Schaefer, E. O. Odera, C. B. Christensen, J. I. Githure, R. W. Olafson, T. G. Theander, et al. 1994. Dichotomy of the human T cell response to *Leishmania* antigens. II. Absent or Th2-like response to gp63 and Th1-like response to lipophosphoglycan-associated protein in cells from cured visceral leishmaniasis patients. *Clin. Exp. Immunol.* 96: 416. KMP-11 is the only antigen that was uniquely recognized by the sera of all asymptomatic *L. infantum* challenged golden hamsters Requena, J. M., M. Soto, M. D. Doria, and C. Alonso. 2000. Immune and clinical parameters associated with *Leishmania infantum* infection in the golden hamster model. *Vet. Immunol. Immunopathol.* 76: 269. Several findings indicate towards a disparate host response to different parasite antigens in cutaneous and visceral forms of leishmaniasis. *Leishmania* glycoprotein-63 (gp63) failed to induce significant IFN-γ from lymphocytes of patients cured from V L Kurtzhals, J. A., A. S. Hey, A. Jardim, M. Kemp, K. U. Schaefer, E. O. Odera, C. B. Christensen, J. I. Githure, R. W. Olafson, T. G. Theander, et al. 1994. Dichotomy of the human T cell response to *Leishmania* antigens. II. Absent or Th2-like response to gp63 and Th1-like response to lipophosphoglycan-associated protein in cells from cured visceral leishmaniasis patients. *Clin. Exp. Immunol.* 96: 416, on the other hand the same antigen, gp63, induced high levels of IFN-γ from lymphocytes of cured Cutaneous Leishmaniasis (CL) patients Kemp, M., A. S. Hey, J. A. Kurtzhals, C. B. Christensen, A. Gaafar, M. D. Mustafa, A. A. Kordofani, A. Ismail, A. Kharazmi, and T. G. Theander. 1994. Dichotomy of the human T cell response to *Leishmania* antigens. I. Th1-like response to *Leishmania* major promastigote antigens in individuals recovered from cutaneous leishmaniasis. *Clin. Exp. Immunol.* 96:410. KMP-11, unlike gp63, induced significant production of IFN-γ from lymphocytes of cured VL patients Kurtzhals, J. A., A. S. Hey, A. Jardim, M. Kemp, K. U. Schaefer, E. O. Odera, C. B. Christensen, J. I. Githure, R. W. Olafson, T. G. Theander, et al. 1994. Dichotomy of the human T cell response to *Leishmania* antigens. II. Absent or Th2-like response to gp63 and Th1-like response to lipophosphoglycan-associated protein in cells from cured visceral leishmaniasis patients. *Clin. Exp. Immunol.* 96: 416. Thus the nature of antigen influencing the host immune response to different *Leishmania* species comes under scrutiny. Hence KMP-11 was selected as a potential DNA vaccine candidate to be tested against experimental visceral leishmaniasis.

A highly conserved membrane protein present in all species of *Leishmania* is selected as the vaccine antigen in form of genetic immunization against visceral leishmananiasis. The membrane protein was cloned from *Leishmania* genome in an expression vector containing CMV promoter for efficient expression in mammalian cells in order to be used as a DNA vaccine construct. Our results show that DNA vaccine using a specific membrane protein was found to be highly protective against both drug-sensitive and drug-resistant forms of *L. donovani* (LD) infection.

A kinetoplastid membrane protein-11 (KMP-11) encoding construct protected extremely susceptible golden hamsters from both pentavalent antimonial responsive (AG83) and antimony resistant (GE1F8R) virulent *L. donovani* challenge.

The KMP-11 nucleotide and polypeptides sequences from *L. donovani* are set forth in SEQ ID NO: 1 and SEQ ID NO: 2, respectively.

All the KMP-11 DNA vaccinated hamsters continued to survive beyond 8 months post infection, with the majority showing sterile protection. Vaccinated hamsters showed reversal of T cell anergy with functional IL-2 generation along with vigorous specific anti-KMP-11 CTL-like response. Cytokines known to influence Th1- and Th2-like immune responses hinted towards a complex immune modulation in presence of a mixed Th1/Th2 response in conferring protection against VL. KMP-11 DNA vaccinated hamsters were protected by a surge in IFN-γ, TNF-α and IL-12 level along with extreme down-regulation of IL-10. Surprisingly the prototype candidature of IL-4, known a disease exacerbating cytokine, was found to have a positive correlation to protection. Contrary to some previous reports, inducible nitric oxide synthase (iNOS) was actively synthesized by macrophages of the protected hamsters with concomitant high levels of NO production. This is the first report of a vaccine conferring protection to both antimony responsive and resistant *Leishmania* strains reflecting several aspects of clinical VL.

The following examples are offered by way of illustration and not by way of limitation. While specific examples have been provided, the above description is illustrative and not restrictive.

Example 1

Preparation of DNA Vaccine Construct 108 promastigotes washed with PBS, pH 7.4, (1.37 mM NaCl, 2.7 mM KCl, 4.3 mM Na2HPO4, 1.47 mM KH2PO4) and STE (10 mM Tris-HCl, pH 7.5, 100 mM NaCl, 1 mM EDTA) were suspended in STE buffer and incubated with Proteinase K (1 mg/ml) (Invitrogen, Grand Island, N.Y.), 0.5% SDS at 50° C. for 4 h. Nucleic acids were extracted by phenol: chloroform: isoamyl alcohol extraction and ethanol precipitation. Genomic DNA was spooled, and subjected to RNase (100 □g/ml) treatment. Genomic DNA from muscles was extracted as described previously Xu, D., and F. Y. Liew. 1995. Protection against leishmaniasis by injection of DNA encoding a major surface glycoprotein, gp63, of *L. major Immunology* 84:173. Whole DNA from all tissues was extracted with Extraction Buffer (10 mM Tris pH 8.0, 0.1 M EDTA, 20 μg/ml pancreatic RNase, 0.5% SDS and 100 μg/ml Proteinase K) followed by phenol: chloroform: isoamyl alcohol extraction and ethanol precipitation method. All the PCR amplification of KMP-11 DNA was done using KMP-11 gene-specific primers: forward primer 5'-ATGGCCACCACGTACGAGGAG-3' (SEQ ID NO: 3) and reverse primer 5'-TTACTTGGACGGGTACTGGGC-3' (SEQ ID NO: 4) with initial denaturation at 94° C. for 5 min followed by 35 cycles of denaturation at 94° C. for 30 s, primer annealing at 60° C. for 30 s, and extension at 72° C. for 30 s.

pCMV-LIC vector used for cloning was purchased from Pharmingen (San Diego, Calif.). KMP-11 gene from *L. donovani* genomic DNA was amplified using High Fidelity Taq™ Polymerase (Invitrogen, Grand Island, N.Y.) having a 3'-5' exonuclease activity. PCR reactions were performed using the following reagents: 50 mM Tris-Cl, 1.5 mM MgCl2 and 100M of each dNTPs (Invitrogen, Grand Island, N.Y.) and KMP-11 specific primers with an additional 13 bp sequence homology to the vector plasmid, forward: 5' CTGGTTCCGGCGAATGGCCACCACGTACGAGGAG 3' (SEQ ID NO: 5); reverse: 5' CTCGCTCCGGCGATTACTTGGACGGGTACTGCGC 3' (SEQ ID NO: 6) for 35 cycles in a Thermocycler (Gene Amp® PCR System 9700, AB Applied Biosciences) under conditions: at 94° C. for 2 min, 94° C. for 30 s, 62° C. for 30 s, and 72° C. for 30 s. Amplified PCR products were electrophoresed in agarose gel and eluted from the gel by GenElute™ Minus EtBr Spin Columns (Sigma, St. Louis, Mo.). For the generation of vector compatible 13 bp single stranded overhangs, 100 □g purified DNA was treated with 5U T4 DNA polymerase (Invitrogen, Grand Island, N.Y.) in a 10 □l reaction volume (165 mM Tris acetate, 330 mM sodium acetate, 50 mM magnesium acetate, 2.5 mM DTT, and 100 □g/ml BSA) in the presence of 0.5 mM dTTP at 37° C. for 20 min. The linear pCMV-LIC (7.5 ng) with 13 bp single-stranded homologous sequence and T4 DNA Polymerase treated PCR products (50 ng) were mixed in 10 □l and allowed for annealing at 22° C. for 30 min. After heat inactivation of T4 DNA polymerase, 5 □l of annealing mix was used to transform competent DH5□ cells. The transformants were screened for the presence of recombinant plasmids with KMP-11 insert by PCR under the similar conditions as mentioned before. Isolated positive clones were sequenced by DNA sequencer (ABI PRISM, model 377).

Control vector without insert was generated by double restriction digest of pCMV-LIC KMP-11 at EcoR1 and Apa1 sites flanking the insert. 2 μg of the construct was initially digested with 10 U EcoR1 at 37° C. in a total volume of 40 μl (500 mM Tris, pH 8.0, 100 mM MgCl2, 500 mM NaCl) followed by 5' end-filling with Klenow fragment in presence of dNTPs in a total volume of 20 μl (0.5 mM dNTP mix, 2 U Klenow fragment) and incubated for 10 min at 37° C. After purification, the DNA was digested with Apa1 at 30° C. for 1 h followed by removal of 3'-overhangs generated by Apa1 a reaction mixture containing purified DNA, 1×T4 DNA Polymerase reaction buffer and 20 μM of each dNTPs were added along with 1 U of T4 DNA polymerase and incubated at 15° C. for 30 min. After heat inactivation of T4 DNA polymerase at 75° C. for 10 min, the DNA was purified as mentioned above. Finally 50 ng linear DNA was ligated by blunt-end ligation in a final volume of 50 μl (250 mM Tris-HCl pH 7.6, 50 mM MgCl2, 5 mM ATP, 5 mM DTT, 25% PEG 8000 solution (w/v), 2 U T4 DNA Ligase) at 14° C. for 24 h. T4 DNA Ligase was inactivated by heating at 70° C. for 10 min. The reaction mixture was used directly for transformation and the colonies negative for KMP-11 was checked by PCR and selected.

Example 2

Verification of DNA Vaccine Encoding Antigen Expression by Transfection

Transfection of Hep2 cell line and normal splenic macrophages derived from golden hamsters were done with pCMV-LIC KMP-11 construct. One day before addition of DNA, 0.9×105 cells per well in 5 ml RPMI 1640 were incubated under normal growth conditions (37° C. and 5% CO2 supply) till the culture was 40% confluent at the time of DNA addition. 0.5 μg of plasmid DNA diluted in DNA Condensation Buffer was mixed with required amount of Enhancer solution according to manufacturer's instruction (Qiagen, GmbH, Hilden, Germany). Cells along with plasmid DNA were incubated at 37° C. in 5% CO2 incubator for 36 h for expression of transfected gene. Two sets of experiment were performed as controls, in one of which the transfection was done with blank-vector (pCMV-LIC) and the other without addition of plasmid DNA.

Example 3

RNA Isolation & RT-PCR from KMP-11 DNA Transfected Hep2 Cells

Total cellular RNA was extracted from 5×106 Hep2 cells by RNeasy Minikit (Qiagen GmbH, Hilden, Germany) and treated with DNase I (Amplification Grade, Invitrogen, Grand Island, N.Y.). RT-PCR was carried out on 500 ng RNA by using Platinum Quantitative RT-PCR Thermoscript One-Step System (Invitrogen, Grand Island, N.Y.) with KMP-11 gene-specific primers: forward primer 5'-ATGGCCAC-CACGTACGAGGAG-3' (SEQ ID NO: 3); and reverse primer 5'-TTACTTGGACGGGTACTGGGC-3' (SEQ ID NO: 4) at the following conditions: 50° C. for 20 min for cDNA synthesis and with initial denaturation at 94° C. for 5 min followed by 35 cycles of denaturation at 94° C. for 30 s, primer annealing at 60° C. for 30 s, and extension at 72° C. for 30 s for PCR in a final volume of 50 □l for amplification of KMP-11 gene (Gene Amp® PCR System 9700 DNA Thermocycler). Amplification of □-actin transcripts as housekeeping control was determined for every PCR sample by amplification with primers specific for □-actin: forward primer 5' ATGGATGATGATATCGCCGAG 3' (SEQ ID NO: 7), reverse primer 5' CATGAAGCAMGCGGTGGAC 3' (SEQ ID NO: 8).

For expression and localization of KMP-11, Hep2 cells (106) were washed thrice by Wash Buffer (PBS, pH 7.4 containing 2% FCS) and incubated in PBS containing 1% BSA at 4° C. for 30 min. Under non-permeabilizing conditions, cells suspended in 50 µl Wash Buffer were stained with 10 µl of primary mouse anti KMP-11-Ab at 4° C. for 45 min in dark. The reaction was stopped by adding 250 µl Wash Buffer and cells were washed thrice followed by incubation with FITC conjugated secondary Ab anti-mouse IgG at 4° C. in dark for 30 min. To check specificity of primary Ab, Hep2 cells were also stained with FITC conjugated anti-mouse IgG only. Finally stained cells were washed thoroughly and suspended in 50 µl of Wash buffer and observed under confocal laser scanning microscope after mounting it in 10% glycerol (LSM 501, Zeiss, Jena, Germany).

Example 4

KMP-11 DNA Vaccination Causes Complete Clearance of Splenic and Hepatic Parasite Burden Following AG83 and GE1F8R Strains of L. donovani Challenge The KMP-11 gene was cloned under CMV promoter in a mammalian expression vector-pCMV-LIC and the expression status of the cloned gene was checked at both the mRNA and protein level by transfecting a human epithelial larynx carcinoma cell line (Hep2) (FIG. 1 A, B, C).

FIG. 1A shows expression of KMP-11 mRNA in Hep2 cells transfected with pCMV-LIC/KMP-11 (lane2) by RT-PCR analysis. Hep2 cells were transfected with pCMV-LIC/KMP-11 construct as described above and RT-PCR was performed from mRNA isolated from transfected Hep2 cells with KMP-11 gene-specific primers and the amplified product compared with øX172 molecular weight marker (Lane 1). β-actin expression as a house-keeping control was determined with specific primers.

FIGS. 1B and 1C displays confocal microscopic picture of Hep2 cells expressing KMP-11 protein after transfection (FIG. 2B) KMP-11 DNA transfected Hep2 cells were immunostained using mouse anti-KMP-11 Ab. Corresponding bright field image is shown in FIG. 2C.

FIG. 1D shows PCR analysis of DNA extracted from muscle (lane1), lymph node (lane2) and spleen (lane3) tissue of hamsters intramuscularly injected with 100 kg of pCMV-LIC/KMP-11 construct. 15 days after plasmid DNA injection total DNA was extracted from muscle, lymph and spleen with extraction buffer and PCR amplification was carried out with KMP-11 gene-specific primers and HGPRT as house keeping gene as described Human cell lines were used instead of hamster cells, as the anti-KMP-11 Ab raised in mouse cross-reacted with hamster cells. Confocal analysis showed that KMP-11 was localized only on the cell surface of Hep2 cells. Since the cells were not detergent-permeabilized prior to antibody staining, we did not find sub-cellular localization of KMP-11 similar to other studies performed under non-permeabilized condition Wang, R., D. L. Doolan, T. P. Le, R. C. Hedstrom, K. M. Coonan, Y. Charoenvit, T. R. Jones, P. Hobart, M. Margalith, J. Ng, W. R. Weiss, M. Sedegah, C. de Taisne, J. A. Norman, and S. L. Hoffman. 1998. Induction of antigen-specific cytotoxic T lymphocytes in humans by a malaria DNA vaccine. Science. 282: 476. Kemp, M., J. A. Kurtzhals, K. Bendtzen, L. K. Poulsen, M. B. Hansen, D. K. Koech, A. Kharazmi, and T. G. Theander. 1993. Leishmania donovani-reactive Th1- and Th2-like T-cell clones from individuals who have recovered from visceral leishmaniasis. Infect. Immun. 61:1069. After intramuscular administration of the expression vector, KMP-11 signals were detected in the muscle, spleen and lymph node tissues of the immunized hamsters 2 wks post-infection by PCR, indicating that the construct is being taken-up by migrating cells and being presented to the squadrons of immune cells in distant lymphoid organs (FIG. 1D).

Figure 2:
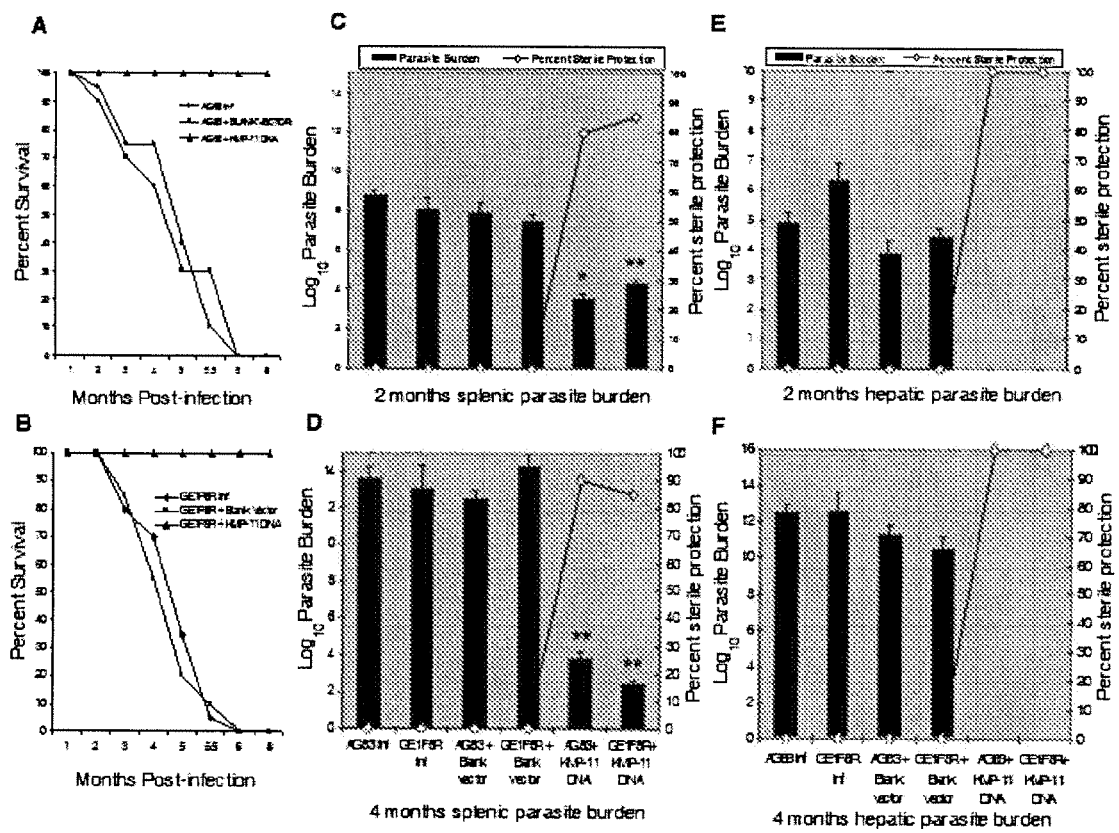
FIG. 2: Sterile protection is induced by KMP-11 DNA immunization against lethal challenge of pentavalent antimonial-sensitive and -resistant virulent strains of *L. donovani*.

To study the efficacy of KMP-11 DNA vaccination in VL, golden hamsters were immunized and challenged with either of two different virulent strains of L. donovani—AG83, a pentavalent antimonial-sensitive strain or GE1F8R, a pentavalent antimonial-resistant strain. All the vaccinated hamsters immunized with KMP-11 DNA survived the lethal challenge of AG83 and GE1F8R and remained healthy until the termination of the experiment at 8 months post-infection, whereas all non-immunized and blank-vector immunized hamsters succumbed to virulent LD challenge within 6 months (FIG. 2 A, B). Remarkably, in all hamsters of both the KMP-11 DNA vaccinated groups, there was complete absence of amastigotes in the impressions of stamp smears of transverse sections of spleens and livers when observed under light microscopy (data not shown). Serial dilution assay confirmed complete sterile protection in the hepatic parasite burden in all of the 20 hamsters in KMP-11 DNA immunized AG83 and GE1F8R challenged groups at 2- and 4-months post-infection (FIG. 2 E, F). Consistently greater than 80% hamsters in both AG83 and GE1F8R challenged KMP-11 DNA vaccinated hamsters showed sterile protection both at 2 and 4 months post-infection with respect to their splenic parasite burden (FIG. 2 C, D). In terms of splenic parasite burden, 16 out of 20 and 18 out of 20 in 2 and 4 months post AG83 challenged, KMP-11 DNA immunized hamsters respectively and 17 out of 20 in both 2 and 4 months post GE1F8R challenged KMP-11 DNA immunized hamsters showed absence of promastigotes in the serially diluted culture till 21 days of observation (data not shown). These KMP-11 DNA vaccinated hamsters failing to show sterile protection showed more than 99% reduction of splenic parasite burden at 2 and 4 months of study when compared to respective blank-vector immunized and infected controls.

FIG. 2 shows sterile protection is induced by KMP-11 DNA immunization against lethal challenge of pentavalent antimonial-sensitive and -resistant virulent strains of L. donovani. Survival kinetics and organ parasite burden of KMP-11 DNA vaccinated hamsters following challenge with either AG83 or GE1F8R compared to respective blank-vector immunized and infected hamsters. For vaccination, hamsters were prophylactically injected twice 7 days apart with 100 μg KMP-11 DNA or empty plasmid DNA through i.m. route. All the infected and DNA immunized hamsters were challenged with either AG83 or GE1F8R (1×106) live promastigotes through intra cardiac route. Organ parasite burden was determined by serial dilution assay. The reciprocal of the highest dilution that was positive for parasite growth was considered to be the concentration of parasite/mg of tissue. Total organ parasite burden was calculated from spleen or liver weight. Results are expressed as log of total organ parasite burden. Data represent the mean±SD for 20 animals per group.

FIGS. 2A and 2B display survival kinetics of KMP-11 DNA vaccinated hamsters challenged either with antimony-sensitive L. donovani strain AG83 (FIG. 2A) or antimony-resistant strain GE1F8R (FIG. 2 B) compared with respective blank-vector immunized and infected control groups of hamsters.

FIGS. 2C and 2D show splenic parasite burden of KMP-11 DNA immunized hamsters challenged either with AG83 or GE1F8R compared with respective blank-vector immunized and infected control groups of hamsters at 2 mo post-infection (FIG. 2 C) and 4 mo post-infection (FIG. 2 D). *, p<0.001 (AG83+KMP-11 DNA vs. AG83 Inf) at 2 mo post infection; **, p<0.0001 in comparison with respective infected control groups. Asterisks represent level of significant variance compared with the groups mentioned.

Figure 3:
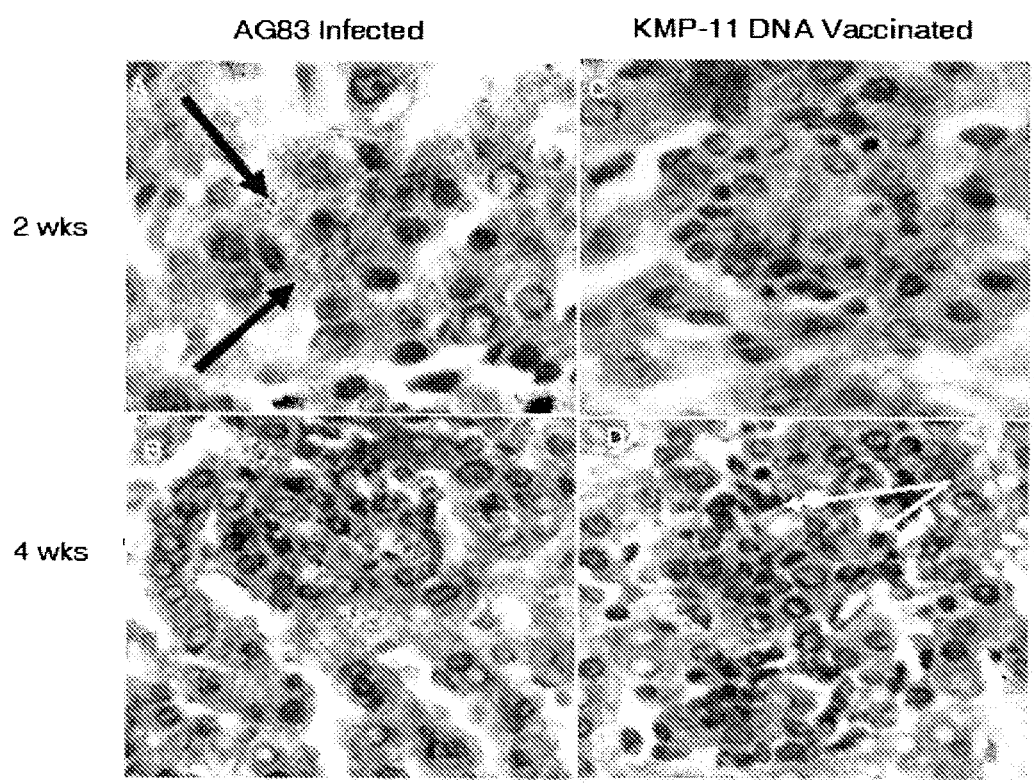
FIG. 3: Early hepatic histologic response to *L. donovani* infected and KMP-11 immunized hamsters.

FIGS. 2E and 2F show hepatic parasite burden of KMP-11 DNA immunized hamsters challenged either with AG83 or GE1F8R compared with respective blank-vector immunized and infected control groups of hamsters at 2 mo post-infection (FIG. 2E) and 4 mo post-infection (FIG. 2F). In terms of liver parasite burden sterile protection was observed for all DNA vaccinated hamsters. Since successful resistance to L. donovani is reflected by early hepatic histological reactions Kemp, M., J. A. Kurtzhals, K. Bendtzen, L. K. Poulsen, M. B. Hansen, D. K. Koech, A. Kharazmi, and T. G. Theander. 1993. Leishmania donovani-reactive Th1- and Th2-like T-cell clones from individuals who have recovered from visceral leishmaniasis. Infect. Immun. 61:1069. Schneemann, M., G. Schoedon, S. Hofer, N. Blau, L. Guerrero, and A. Schaffner. 1993. Nitric oxide synthase is not a constituent of the antimicrobial armature of human mononuclear phagocytes. J. Infect. Dis. 167:1358. Bhakuni, V., S. Kulkarni, V. Ali, U. K. Singh, H. B. Levy, and R. K. Maheshwari. 1999. Immunochemotherapy for Leishmania donovani infection in golden hamsters: combinatorial action of poly ICLC plus L-arginine and sodium stibogluconate (Stibanate). J. Interferon. Cytokine. Res. 19:1103. Green, S. J., R. M. Crawford, J. T. Hockmeyer, M. S. Meltzer, and C. A. Nacy. 1990. Leishmania major amastigotes initiate the L-arginine-dependent killing mechanism in IFN-gamma-stimulated macrophages by induction of tumor necrosis factor-alpha. J. Immunol. 145: 4290, the liver sections of AG83 and GE1F8R infected and KMP-11 DNA vaccinated hamsters were examined. In 2 weeks time, parasitized Kupffer cells were seen with few surrounding mononuclear cells and infiltrating lymphocytes in both AG83 (FIG. 3A) and GE1F8R (data not shown) infected hamsters. By 4 weeks, heavily parasitized Kupffer cells were seen with congregation of cells surrounding parasitized core forming a granuloma like structure but with few infiltrating lymphocytes (FIG. 3 B). In KMP-11 DNA vaccinated hamsters, parasitized Kupffer cells were not observed and well formed granuloma comprised of mononuclear cells and surrounding lymphocytes were observed at 2 weeks post-infection (FIG. 3 C). In 4 weeks time, complete absence of parasitized Kupffer cells with higher number of lymphocyte infiltrates was observed (FIG. 3 D).

FIG. 3 shows early hepatic histologic response to L. donovani infected and KMP-11 immunized hamsters. Magnification: (A-D) 40×. FIG. 3A: 2 wks after infection parasitized Kupffer Cells (large black arrows) with few epitheloid cells resemble ill-formed granuloma. FIG. 3B: 4 wks after infection, granuloma is more organized with heavily parasitized Kupffer cells and few infiltrating lymphocytes. FIG. 3C: In contrast, 2 wks after infection DNA immunized hamsters show well organized granuloma free of parasites with surrounding epitheloid cells and lymphocyte. FIG. 3D: 4 wks after infection more infiltrating lymphocytes (small white arrows) are seen in an enlarged structure resembling involuting granuloma.

Example 5

Soluble Leishmanial Antigen (SLA) Induces Proliferation of Splenocytes and IL-2 Generation from KMP-11 DNA Vaccinated Hamsters Impairment of cell mediated immune response in active VL patients is reflected by marked T cell anergy specific to Leishmania antigens as found in Indian Kala-azar and South American VL as well as in experimental models Haldar, J. P., S. Ghose, K. C. Saha, and A. C. Ghose. 1983. Cell-mediated immune response in Indian kala-azar and post-kala-azar dermal leishmaniasis. Infect. Immun. 42: 702. Carvalho, E. M., O. Bacellaro, C. Brownell, T. Regis, R. L. Coffinan, and S. G. Reed. 1994. Restoration of IFN-gamma production and lymphocyte proliferation in visceral leishmaniasis. J. Immunol. 152:5949. Gifawesen, C., and J. P. Farrell. 1989. Comparison of T-cell responses in self-limiting versus progressive visceral Leishmania donovani infections in golden hamsters. Infect. Immun. 57:3091. As it is generally noted that in vitro T cell proliferation is impaired in VL, a T cell proliferation assay was performed.

Splenocytes from AG83 challenged KMP-11 DNA vaccinated hamsters 90 days post-infection showed about 17-fold enhanced proliferation than infected and blank-vector immunized hamsters at 5 μg SLA concentration. At a similar antigen concentration, GE1F8R challenged KMP-11 DNA vaccinated animals showed about 13 times greater proliferation compared to infected and blank-vector immunized hamsters (FIG. 4 A).

It has been shown that impairment of IL-2 generation and depressed splenic T cell response are associated in experimental as well as clinical V L Carvalho, E. M., R. Badaro, S. G. Reed, T. C. Jones, and W. D. Johnson, Jr. 1985. Absence of g interferon and interleukin 2 production during active visceral leishmaniasis. J. Clin. Invest. 76:2066. Carvalho, E. M., O. Bacellaro, C. Brownell, T. Regis, R. L. Coffinan, and S. G. Reed. 1994. Restoration of IFN-gamma production and lymphocyte proliferation in visceral leishmaniasis. J. Immunol. 152:5949. Cohen, A. D., J. D. Boyer, and D. B. Weiner. 1998. Modulating the immune response to genetic immunization. FASEB J. 12: 1611. Thus we addressed the functional activity of IL-2 in KMP-11 DNA immunized and infected hamsters. When spleen cells from all groups hamster 90 days post infection were stimulated with and without SLA for 24 h and the supernatants were tested for IL-2 activity (in terms of 3H-thymidine uptake in HT2 cell line), it was seen that the culture supernatants from splenocytes of KMP-11 DNA immunized hamsters contained significant level of IL-2 compared to normal as well as infected hamsters (FIG. 4 B). In case of AG83 infection, KMP-11 DNA vaccinated hamsters showed 3.66 ($p<0.001$), 5.16 ($p<0.0001$) and 2.82 ($p<0.0005$) fold more IL-2 production at 0.5, 5, 50 µg/ml SLA concentration respectively, than corresponding infected group, whereas, DNA immunized GE1F8R infected hamsters showed about 3.57 ($p<0.001$), 7.69 ($p<0.0001$), 2.52 ($p>0.0005$) fold more IL-2 production at 0.5, 5, 50 µg/ml SLA concentration respectively, than corresponding infected hamsters. KMP-11 DNA vaccinated hamster splenocytes showed insignificant level of IL-2 production without SLA stimulation ($p>0.05$).

Figure 4:
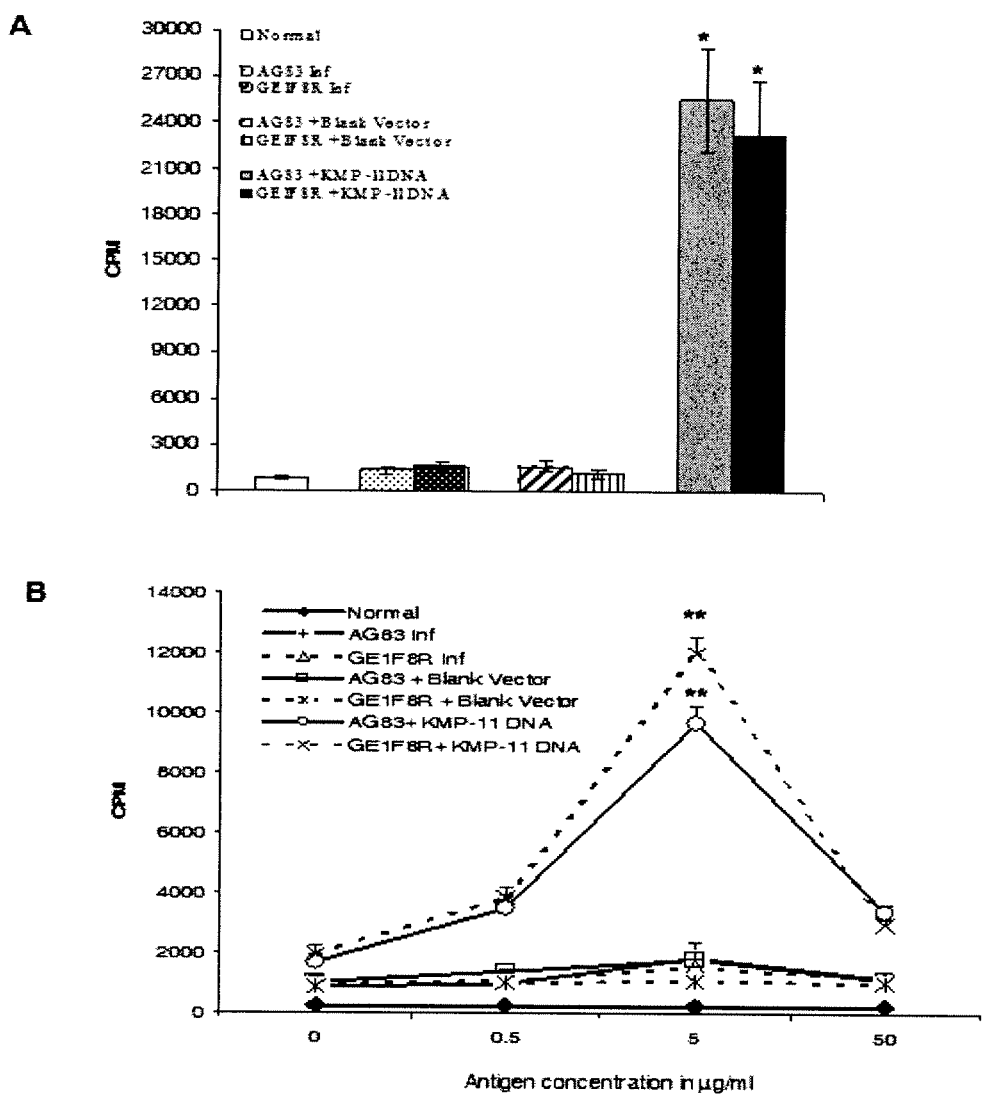
FIG. 4: KMP-11 DNA vaccination overcomes impaired T cell proliferation with significant IL-2 production.

FIG. 4 shows KMP-11 DNA vaccination overcomes impaired T cell proliferation with significant IL-2 production. FIG. 4A: Proliferative response to SLA (5 µg/ml) by splenocytes from KMP-11 DNA immunized hamsters either challenged with AG83 or GE1F8R compared with respective blank-vector immunized and infected control. Proliferation was measured by 3H-thymidine incorporation. At 5 µg/ml SLA stimulation *, $p<0.0005$ for (AG83+KMP-11 DNA vs. AG83 Inf) and (GE1F8R+KMP-11 DNA vs. GE1F8R Inf). The results are representative of 4 individual experiments (n=5/group) and data represent the mean of triplicate wells I SE.

FIG. 4B: Production of IL-2 by spleen cells from KMP-11 DNA immunized hamsters challenged with either AG83 or GE1F8R compared with respective blank-vector immunized and infected control in terms of proliferation of an IL-2 dependent murine cell line HT2, i.e. proportional to 3H-thymidine incorporation. The results are representative of 4 individual experiments (n=5/group) and data represent the mean of triplicate wells ±SE. At 5 µg/ml SLA stimulation **, $p<0.0001$ for (AG83+KMP-11 DNA vs. AG83 Inf) and (GE1F8R+KMP-11 DNA vs. GE1F8R Inf)

Example 6

Figure 5:
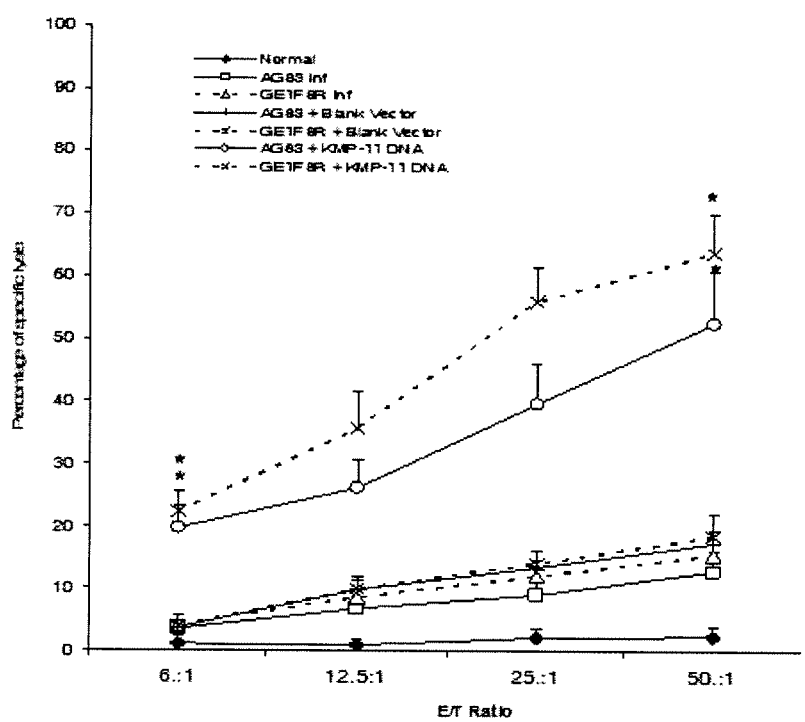
FIG. 5: KMP-11 DNA immunization generates anti KMP-11 Cytotoxic T Lymphocyte like response.

Immunization with KMP-11 DNA Generates Anti-KMP-11 CTL-Like Response in Vaccinated Hamsters Intramuscular administration of expression plasmid construct carrying antigen cDNA resulted in activation of antigen specific CTLs due to their MHC class I mediated processing and CTL priming as shown against several viral proteins Cohen, A. D., J. D. Boyer, and D. B. Weiner. 1998. Modulating the immune response to genetic immunization. *FASEB J.* 12: 1611 and also against malarial circumsporozoite protein tested in human volunteers Wang, R., D. L. Doolan, T. P. Le, R. C. Hedstrom, K. M. Coonan, Y. Charoenvit, T. R. Jones, P. Hobart, M. Margalith, J. Ng, W. R. Weiss, M. Sedegah, C. de Taisne, J. A. Norman, and S. L. Hoffman. 1998. Induction of antigen-specific cytotoxic T lymphocytes in humans by a malaria DNA vaccine. *Science.* 282: 476. We thus became interested to see whether the effector mechanism involves specific CTL-like response against KMP-11 in addition to generation of T-helper response. Earlier observation that CD8+T cell depletion at time of infection resulted in abrogated protective efficacy of LACK-DNA vaccination in murine CL model suggested about a DNA vaccination induced dominant role of CD8+T cell mediated protective immune response Gurunathan, S., D. L. Sacks, D. R. Brown, S. L. Reiner, H. Charest, N. Glaichenhaus, and R. A. Seder. 1997. Vaccination with DNA encoding the immunodominant LACK parasite antigen confers protective immunity to mice infected with *Leishmania major. J. Exp. Med.* 186:1137. In our case SLA stimulated splenocytes for 7 days from KMP-11 DNA immunized hamsters (105 days post-infection) challenged with either AG83 or GE1F8R showed a 52.5% and 63.7% lysis of 51Cr-labeled KMP-11 transfected autologous splenic macrophages respectively at 50:1 E/T ratio (FIG. 5). The infected and blank-vector immunized control hamsters showed less than 17% lysis of labeled targets at 50:1 E/T ratio and did not differ significantly between AG83 and GE1F8R challenged hamsters. This basal level of lysis in the infected and blank-vector immunized infected hamsters might indicate towards the presence of a low marginal threshold of anti-KMP-11 specific cytotoxic T lymphocyte like response even at acute stage of infection that might not be sufficient to bring about protective response. Although in hamsters CTLs have not been characterized, we consider the phenomenon akin to the prototype CTL generation known in other experimental models. This was further corroborated by the failure of the non-adherent splenic T cells to lyse autologous macrophages transfected with Enhanced Green Fluorescent Protein (EGFP) expressing pEFGP-N1 construct validating KMP-11 specificity of the cytotoxic cells generated in vaccinated hamster splenocytes (data not shown).

FIG. 5 shown KMP-11 DNA immunization generates anti KMP-11 Cytotoxic T Lymphocyte like response. Splenocytes (Effector) from different groups of hamsters were pulsed with SLA for 7 days. Only adherent splenocytes were cultured and labeled with 51Cr after transfecting with pCMV-LIC/KMP-11 or pCMV-LIC plasmid DNA and used as target. Target cells were autologous macrophages derived from splenocytes of normal hamsters. Macrophages transfected with unrelated expression plasmid did not show more than 10% lysis (data not shown). Spontaneous release was less than 15%. Results are representative of 5 individual experiments (n=5/group) and data represent the mean±SE. At 50:1 and 6:1 E/T ratio both groups of DNA immunized hamsters showed *, $p<0.0001$ in comparison with respective infected control groups.

Example 7

Figure 6:
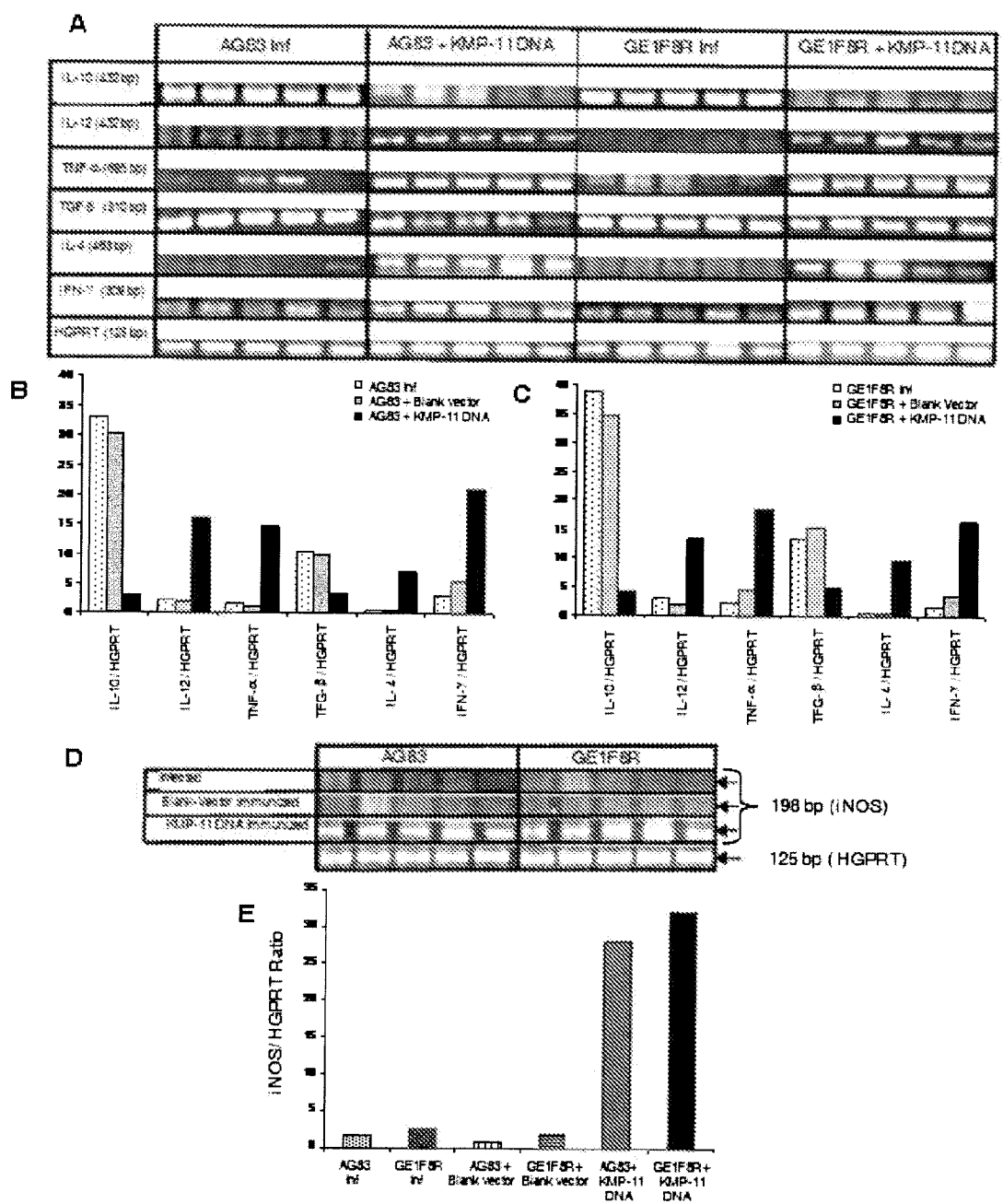
FIG. 6: Protected KMP-11 DNA vaccinated hamsters produce both Th1 and Th2 cytokines with significant iNOS transcript generation.

DNA Immunization Elicits a Mixed Th1- and Th2-Like Response in Protected Group of Hamsters As in *L. donovani* infected murine models, a mixed Th1 and Th2 response has been noted in VL patients cured from the disease Kaye, P. M., A. J. Curry, and J. M. Blackwell. 1991. Differential production of Th1- and Th2-derived cytokines does not determine the genetically controlled or vaccine-induced rate of cure in murine visceral leishmaniasis. *J Immunol* 146: 2763. Kemp, K., M. Kemp, A. Kharazmi, A. Ismail, J. A. Kurtzhals, L. Hviid, and T. G. Theander. 1999. *Leishmania*-specific T cells expressing interferon-gamma (IFN-gamma) and IL-10 upon activation are expanded in individuals cured of visceral leishmaniasis. *Clin. Exp. Immunol.* 116: 500. Kemp, K. 2000. Cytokine-producing T cell subsets in human leishmaniasis. Arch. *Immunol. Ther. Exp.* (Warsz). 48:173. Kemp, M., J. A. Kurtzhals, K. Bendtzen, L. K. Poulsen, M. B. Hansen, D. K. Koech, A. Kharazmi, and T. G. Theander. 1993. *Leishmania donovani*-reactive Th1- and Th2-like T-cell clones from individuals who have recovered from visceral leishmaniasis. *Infect. Immun.* 61:1069. We made a detailed splenic cytokine analysis at 105 days post infective period as VL is at an acutely progressive stage at this time point. Comparative cytokine profile showed that in both groups of vaccinated hamsters expression of IFN-γ transcripts were about 7- and 10-folds greater in AG83 and GE1F8R infected and blank-vector immunized control hamsters respectively (FIG. 6 A, B, C). IL-12 transcripts in KMP-11 DNA vaccinated hamsters were 7.2- and 4.7-folds greater than in AG83 and GE1F8R infected and blank-vector immunized control hamsters respectively. Level of expression of Th1 suppressive cytokine, IL-10 was 11- and 10-folds more in AG83 and GE1F8R infected groups respectively than corresponding vaccinated groups of hamster reflecting its extreme down-regulation. TNF-α showed 9 and 8.71 folds increased expression in KMP-11 DNA vaccinated groups compared to AG83 and GE1F8R infected and blank-vector immunized control groups of hamster. Expression of TGF-β was moderate in both the infected groups whereas in case of KMP-11 DNA vaccinated hamsters its expression was significantly down regulated. Intriguingly, expression of an established Th2 cytokine like IL-4 showed ubiquitous association with the protection showing copious transcript generation from the spleen of both AG83 and GE1F8R challenged and KMP-11 DNA immunized protected groups of hamsters. IL-4 transcript was mostly undetectable in both infected and blank-vector immunized hamsters. KMP-11 DNA immunized hamsters infected with AG83 and GE1F8R showed nearly 15- and 16.4-folds increased IL-4 transcript generation than respective infected and blank-vector control groups. Apparently KMP-11 DNA vaccination conferred protection by the preferential induction of Th1 and Th2 like cytokine genes to generate anti-leishmanial immune response as absolute dominance of Th1- or Th2-like cytokine genes conferring protection or susceptibility could not be highlighted.

FIG. 6 shows DNA Immunization Induces iNOS Transcript in KMP-11 DNA Vaccinated Hamsters. Lack of detectable NO due to an impaired iNOS signaling pathway despite significant production of IFN-γ is attributed to increased susceptibility to L. donovani infection in both hamster and human macrophages Melby, P. C., B. Chandrasekar, W. Zhao, and J. E. Coe. 2001. The hamster as a model of human visceral leishmaniasis: progressive disease and impaired generation of nitric oxide in the face of a prominent Th1-like cytokine response. J. Immunol. 166: 1912. Schneemann, M., G. Schoedon, S. Hofer, N. Blau, L. Guerrero, and A. Schaffner. 1993. Nitric oxide synthase is not a constituent of the antimicrobial armature of human mononuclear phagocytes. J. Infect. Dis. 167:1358. In case of KMP-11 DNA immunized AG83 challenged hamsters we found a 17-fold higher expression of iNOS transcript, whereas DNA immunized GE1F8R challenged showed a 13.2-fold increase with respect to their infected controls at 105 days post-infection (FIG. 6 D, E). iNOS transcripts could not be readily detected from splenic macrophages of blank-vector immunized or infected hamsters. Previously iNOS activation and NO-mediated leishmanicidal activity was implicated in L. donovani challenged golden hamsters treated with poly ICLC and L-arginine that was inhibited by N w nitro-L-arginine (N w NLA)—an inhibitor of iNOS (30). Our finding is commensurate with extremely elevated IFN-γ and TNF-α transcripts produced from the splenocytes of the KMP-11 DNA vaccinated hamsters. This experiment has revealed, for the first time, that iNOS expression which is impaired in L. donovani infected experimental hamster model can be elicited by genetic immunization with KMP-11.

FIG. 6 illustrates that Protected KMP-11 DNA vaccinated hamsters produce both Th1 and Th2 cytokines with significant iNOS transcript generation.

FIG. 6A, B, C: Cytokine profile analysis of KMP-11 DNA immunized hamsters challenged with either AG83 or GE1F8R compared with respective infected control groups by Semi-quantitative RT-PCR and Densitometry. 5 representative hamsters from each experimental group were randomly picked to analyze the splenic cytokine profile. Agarose gel picture of cytokine RT-PCR profile of normal, blank-vector immunized and AG83 or GE1F8R infected hamster are not shown in this figure. Equivalent numbers of cells were taken for RNA isolation and equal amounts of RNA were used as input in RT-PCR. In all the cases HGPRT was used as house keeping gene control. Bar diagram in the FIG. (6B & 6C) shows the densitometry analysis of mRNA expression. Expression of each cytokine transcripts were expressed as ratio of cytokine mRNA to HGPRT mRNA. FIGS. 6D and E: Semi-quantitative RT-PCR and densitometry analysis of iNOS transcripts produced from purified splenic macrophages of KMP-11 DNA immunized hamsters challenged with either AG83 or GE1F8R compared with respective blank-vector immunized and infected control. Expression of iNOS transcripts were expressed as ratio of iNOS mRNA to HGPRT mRNA. Results are representative of 5 individual experiments (n=5/group).

Example 8

RNI and ROS Generation in KMP-11 DNA Vaccinated Hamsters

Figure 7:
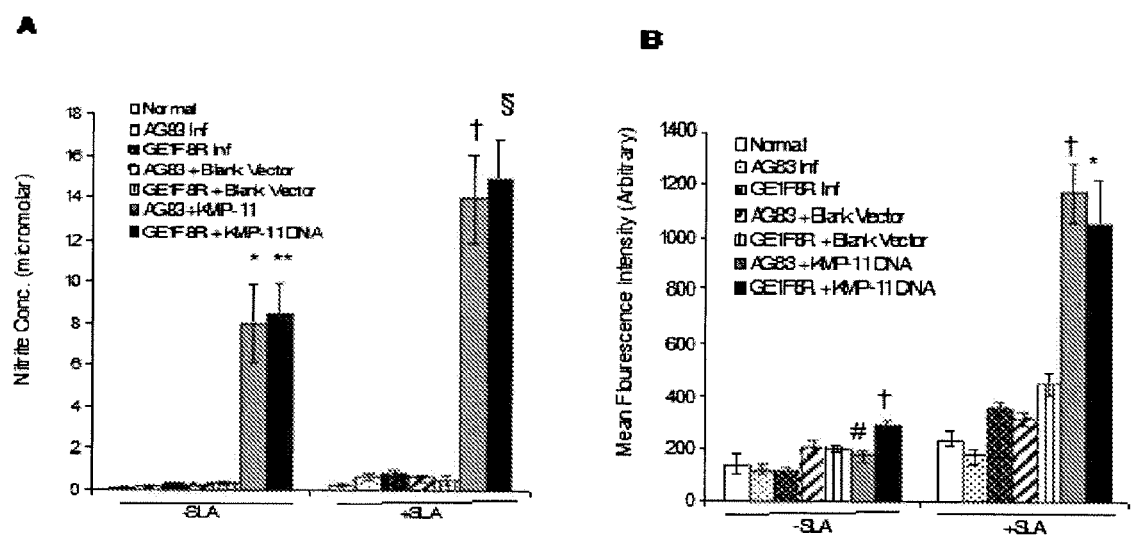
FIG. 7: Production of leishmanicidal effector molecules in KMP-11 DNA immunized hamsters.

Nitrite and superoxides are two macrophage-derived oxidants that are critical in controlling Leishmania infection Melby, P. C., B. Chandrasekar, W. Zhao, and J. E. Coe. 2001. The hamster as a model of human visceral leishmaniasis: progressive disease and impaired generation of nitric oxide in the face of a prominent Th1-like cytokine response. J Immunol. 166: 1912. Green, S. J., R. M. Crawford, J. T. Hockmeyer, M. S. Meltzer, and C. A. Nacy. 1990. Leishmania major amastigotes initiate the L-arginine-dependent killing mechanism in IFN-gamma-stimulated macrophages by induction of tumor necrosis factor-alpha. J. Immunol. 145:4290. Liew, F. Y., Y. Li, and S. Millott. 1990. Tumor necrosis factor-alpha synergizes with IFN-gamma in mediating killing of Leishmania major through the induction of nitric oxide. J. Immunol. 145:4306. Liew, F. Y., Y. Li, and S. Millott. 1990. Tumour necrosis factor (TNF-alpha) in leishmaniasis. II. TNF-alpha-induced macrophage leishmanicidal activity is mediated by nitric oxide from L-arginine. Immunology. 71:556. Wei, X. Q., I. G. Charles, A. Smith, J. Ure, G. J. Feng, F. P. Huang, D. Xu, W. Muller, S. Moncada, F. Y. Liew. 1995. Altered immune responses in mice lacking inducible nitric oxide synthase. Nature. 375:408. In cytokine expression profile of both infected and vaccinated hamsters we got elevated level of iNOS transcripts along with high TNF-α and IFN-γ transcripts in protected hamsters. Thus we became interested to know whether these two cytokines can activate macrophages to an extent where it has sufficient stimuli to generate NO in a down-regulated IL-10 environment. Moreover a recent report showed in an ex vivo study where superior efficacy of SLA in production of IFN-γ and TNF-α compared to LACK antigen alone was demonstrated Perez-Victoria, J. M., F. J. Perez-Victoria, A. Parodi-Talice, I. A. Jimenez, A. G. Ravelo, S. Castanys, and F. Gamarro. 2001. Alkyl-lysophospholipid resistance in multidrug-resistant Leishmania tropica and chemosensitization by a novel P-glycoprotein-like transporter modulator. Antimicrob. Agents Chemother. 45(9): 2468. This prompted us to study the production of NO and ROS (Reactive Oxygen Species) both with and without SLA stimulation. At 3 various SLA concentrations tested (0.5, 5, 50) optimum ROS and NO production was found at 5 μg/ml (data not shown). We found that at 105 days post-infection, AG83 infected hamsters in presence of SLA stimulation showed 0.7 µM nitrite production and the GE1F8R challenged hamsters showed 0.84 µM nitrite production (FIG. 7 A). AG83 challenged KMP-11 DNA vaccinated hamsters showed near 20-fold (14 µM) increase in nitrite production and GE1F8R challenged KMP-11 DNA vaccinated hamsters showed 15 µM nitrite when stimulated 5 µg/ml of SLA. Remarkably significant NO generation was detected from splenocytes of vaccinated hamsters (but not from infected and blank-vector immunized hamsters) even in absence of SLA stimulation. Reactive Nitrogen Intermediates (RNI) like NO is itself sufficient to clear *L. donovani* infection although ROS contributes to the efficiency of parasite killing Shiloh, M. U., J. D. MacMicking, S. Nicholson, J. E. Brause, S. Potter, M. Marino, F. Fang, M. Dinauer, and C. Nathan. 1999. Phenotype of mice and macrophages deficient in both phagocyte oxidase and inducible nitric oxide synthase. *Immunity*. 10: 29. Fang, F. C. 1997. Perspectives series: host/pathogen interactions. Mechanisms of nitric oxide-related antimicrobial activity. *J. Clin. Invest.* 99: 2818. In presence of SLA stimulation both AG83 and GE1F8R challenged DNA vaccinated groups showed nearly 6- and 3-folds increase in production of superoxide respectively than corresponding infected controls reflecting the overall activated state of the splenic macrophages specific to *Leishmania* antigen (FIG. 7 B).

FIG. 7 shows production of leishmanicidal effector molecules in KMP-11 DNA immunized hamsters. FIG. 7A: Nitrite generation by supernatants of splenocytes (devoid of RBC) derived from blank-vector and KMP-11 DNA immunized hamsters challenged with either AG83 or GE1F8R and respective infected controls stimulated with SLA (5 µg/ml) or without SLA for 72 h. Without SLA stimulation, *, $p<0.005$ (AG83+KMP-11 DNA vs. AG83 Inf); **, $p<0.002$ (GE1F8R+KMP-11 DNA vs. GE1F8R Inf).

With SLA stimulation, †, $p<0.0005$ (AG83+KMP-11 DNA vs. AG83 Inf) and §, $p<0.0001$ (GE1F8R+KMP11 DNA vs. GE1F8R Inf).

Results are representative of 5 experiments (n=5/group) and data represent the mean±SE. FIG. 7 B: ROS generation measured by H2DCFDA staining of the splenocytes (devoid of RBC) from different experimental groups of hamsters with and without SLA stimulation for 72 h. Without SLA stimulation, #, $p<0.5$(AG83+KMP-11 DNA vs. AG83 Inf), t, $p<0.0005$ (GE1F8R+KMP11 DNA vs. GE1F8R Inf).

With SLA stimulation, †, $p<0.0005$ (AG83+KMP-11 DNA vs. AG83 Inf) and *, $p<0.005$ (GE1F8R+KMP11 DNA vs. GE1F8R Inf). Data represent the mean±SE (n=5/group) and results are representative of 3 experiments.

Example 9

Figure 8:
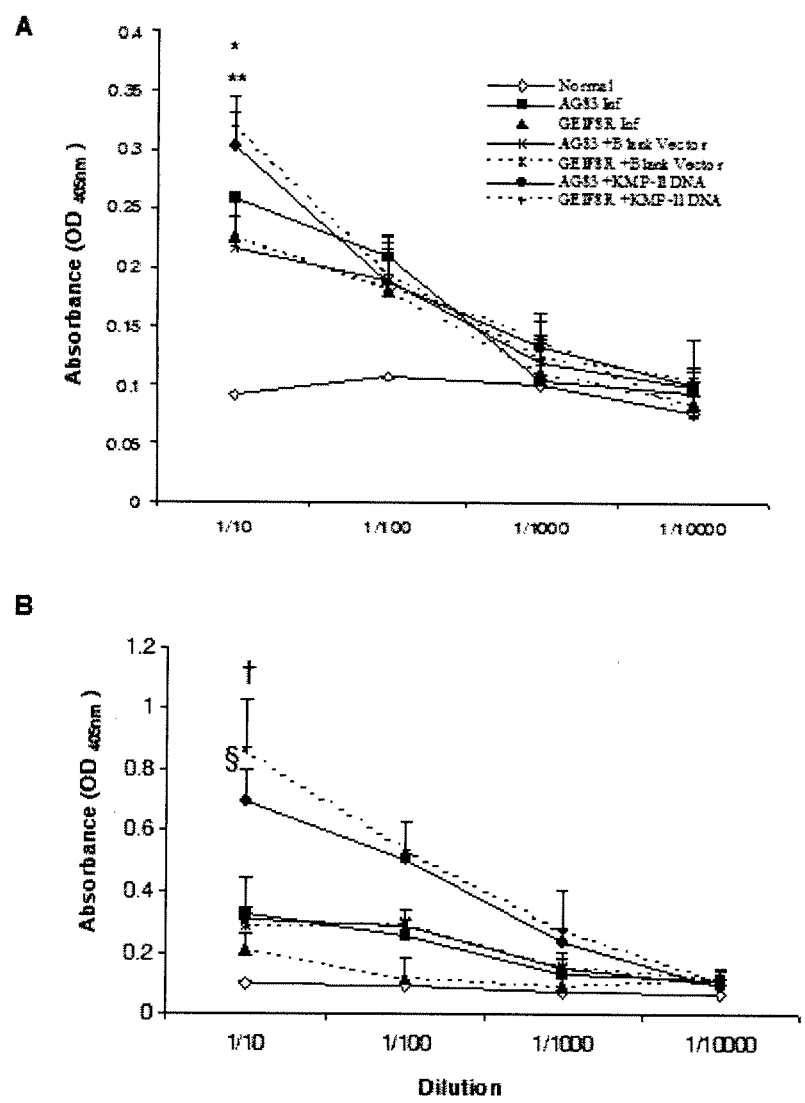
FIG. 8: Anti-KMP-11 IgG1 and IgG2 Ab titers in infected and KMP-11 DNA vaccinated hamsters.

KMP-11 Specific Production of IgG1 and IgG2 are Increased in Vaccinated Hamsters Challenged with AG83 and GE1F8R In mouse IL-4 and IFN-γ are two cytokines that direct immunoglobulin class switching of IgG1 and IgG2a respectively. Though in hamsters there are no distinct classifications of immunoglobulin, it is believed that hamster IgG2 corresponds to mouse IgG2a/IgG2b and hamster IgG1 corresponds to murine IgG1 Melby, P. C., B. Chandrasekar, W. Zhao, and J. E. Coe. 2001. The hamster as a model of human visceral leishmaniasis: progressive disease and impaired generation of nitric oxide in the face of a prominent Th1-like cytokine response. *J. Immunol.* 166: 1912. We measured KMP-11 specific production of these Ab specific isotypes. DNA vaccinated hamsters developed an effective immune response by showing substantially higher levels of KMP-11 specific levels of IgG2 Ab titer which is a measure of cell-mediated immune response (FIG. 8 B). Although highly significant difference was found in IgG2 titer between KMP-11 DNA vaccinated and infected control groups of hamsters ($p<0.0001$), there was no significant difference in the KMP-11 specific IgG1 levels ($P<0.5$) among the infected and the vaccinated hamsters (FIG. 8 A). This insignificant difference of IgG1 titer between KMP-11 DNA vaccinated and infected control hamster sera might be due to enhanced IL-4 production associated with the vaccinated protected animals.

FIG. 8 shows anti-KMP-11 IgG1 and IgG2 Ab titers in infected and KMP-11 DNA vaccinated hamsters. Sera from KMP-11 DNA and blank-vector immunized hamsters challenged with either AG83 or GE1F8R and respective infected controls (n=5/group) were analyzed individually for KMP-11 specific anti-IgG1 and IgG2 antibody titers by ELISA. The results are representative of 3 experiments and data represent the mean±SE. In case IgG1*, $p<0.5$ (AG83+KMP-11 DNA vs. AG83 Inf); **, $p<0.1$ (GE1F8R+KMP11 DNA vs. GE1F8R Inf) which are not statistically significant. But with respect to normal $p<0.0005$ (Normal vs. AG83 Inf), $p<0.01$ (Normal vs. GE1F8R Inf), $p<0.0001$ (AG83+KMP-11 DNA vs. AG83 Inf & GE1F8R+KMP11 DNA vs. GE1F8R Inf), which are highly significant. In case of IgG2 †, $p<0.05$ (AG83+KMP-11 DNA vs. AG83 Inf) and §, $p<0.005$ (GE1F8R+KMP11 DNA vs. GE 1F8R Inf).

What is claimed is:

1. A method for immunizing a mammal against visceral *Leishmania*, comprising administering to the mammal a DNA vaccine comprising a mammalian expression vector comprising cDNA encoding a Kinetoplastid Membrane Protein-11 (KMP-11) antigen before virulent *Leishmania* parasite exposure or infection, wherein
   (1) the antigen is a cell surface membrane protein from a virulent form of *Leishmania*;
   (2) the antigen confers protection from the parasite; and
   (3) the vaccine confers sterile protection in tissues that would be infected by a virulent form of *Leishmania* upon exposure.

2. The method of claim 1, wherein the virulent *Leishmania* is *L. donovani*.

3. The method of claim 1, wherein the infected mammal is a Syrian hamster.

4. The method of claim 1, wherein the vaccine stimulates a CD8+ cytotoxic T cell response.

5. The method of claim 1, wherein the antigen is an immunogenic polypeptide.

6. A method for immunizing a mammal harboring a lethal dose of virulent *Leishmania* infection against visceral *Leishmania*, comprising:
   administering to the infected mammal a DNA vaccine comprising a mammalian expression vector comprising a nucleotide sequence encoding a membrane protein of *Leishmania* parasites consisting of an antigen known as Kinetoplastid Membrane Protein-11 (KMP-11)
   wherein (1) the antigen comprises a cell surface protein of *Leishmania*; (2) the antigen prevents mortality of the mammal from lethal virulent *Leishmania* infection; and (3) the vaccine confers sterile protection in tissues that would be infected by *Leishmania* upon exposure.

7. The method of claim 6, wherein the virulent *Leishmania* is *L. donovani*.

8. The method of claim 6, wherein the tissues are selected from the group consisting of spleen and liver.

9. The method of claim 6, wherein the DNA vaccine encodes an immunogenic polypeptide.

10. The method of claim 1, wherein the tissues are selected from the group consisting of spleen and liver.

* * * * *